United States Patent
Qian et al.

(10) Patent No.: US 10,762,168 B2
(45) Date of Patent: Sep. 1, 2020

(54) REPORT VIEWER USING RADIOLOGICAL DESCRIPTORS

(75) Inventors: Yuechen Qian, Briarcliff Manor, NY (US); Sevenster Merlijn, Chicago, IL (US); Giselle Rebecca Isner, Bronx, NY (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 730 days.

(21) Appl. No.: 13/641,901

(22) PCT Filed: Mar. 29, 2011

(86) PCT No.: PCT/IB2011/051338
§ 371 (c)(1),
(2), (4) Date: Feb. 6, 2013

(87) PCT Pub. No.: WO2011/132097
PCT Pub. Date: Oct. 27, 2011

(65) Prior Publication Data
US 2014/0149407 A1  May 29, 2014

Related U.S. Application Data

(60) Provisional application No. 61/325,640, filed on Apr. 19, 2010.

(51) Int. Cl.
*G06F 16/35*  (2019.01)
*G06F 19/00*  (2018.01)
(Continued)

(52) U.S. Cl.
CPC .......... *G06F 19/32* (2013.01); *G06F 16/3331* (2019.01); *G06F 16/35* (2019.01);
(Continued)

(58) Field of Classification Search
CPC ......... G06F 17/30634; G06F 17/30657; G06F 17/30705; G06F 17/30716; G06F 19/32;
(Continued)

(56) References Cited

U.S. PATENT DOCUMENTS 5,729,620 A   3/1998  Wang
6,477,262 B2  11/2002 Wang
(Continued)

FOREIGN PATENT DOCUMENTS

JP   2008253551 A   10/2008

OTHER PUBLICATIONS

Thomas Wittenberg, Matthias Elter and Rudiger Schulz-Wendtland. "Complete Digital Iconic and Textual Annotation for Mammography". Bildverarbeitung Fur Die Medizin 2007. Informatik aktuell, 2007, 3., 91-95, DOI: 10.1007/978-3-540-71091-2_19.

*Primary Examiner* — Hares Jami

(57) ABSTRACT

A method and a report viewer for viewing a structured report, such as medical report describing radiological images using descriptors selected from a predefined list of descriptors, includes the acts of opening the medical report; and in response to the opening act, searching for a further report related to the descriptors of the medical report, and highlighting words and/or sentences in the further report that match keywords derived from the descriptors. The medical report and the further report may be displayed simultaneously with the words and/or sentences being highlighted. The further report may include an unstructured text report, and the method further includes mapping the descriptors to findings in the text report and highlighting the findings.

20 Claims, 11 Drawing Sheets

(51) Int. Cl.
*G06F 16/33* (2019.01)
*G16H 50/70* (2018.01)
*G16H 15/00* (2018.01)

(52) U.S. Cl.
CPC .......... *G06F 19/321* (2013.01); *G16H 15/00* (2018.01); *G16H 50/70* (2018.01)

(58) Field of Classification Search
CPC . G06F 19/321; G06F 19/3443; G06F 19/3487
USPC .......................................... 707/736, 737, 758
See application file for complete search history.

(56) References Cited

U.S. PATENT DOCUMENTS

| | | | |
|---|---|---|---|
| 7,844,089 B2 * | 11/2010 | Kanada | G06F 19/321 |
| | | | 382/128 |
| 8,320,651 B2 | 11/2012 | Vining et al. | |
| 8,521,561 B2 | 8/2013 | Sasai et al. | |
| 2005/0096530 A1 | 5/2005 | Daw et al. | |
| 2005/0273365 A1 | 12/2005 | Baumgartner et al. | |
| 2006/0136259 A1 | 6/2006 | Weiner et al. | |
| 2006/0147099 A1 | 7/2006 | Marshall et al. | |
| 2006/0242143 A1 * | 10/2006 | Esham | G06F 19/321 |
| 2007/0237377 A1 * | 10/2007 | Oosawa | G06F 19/321 |
| | | | 382/128 |
| 2008/0004505 A1 | 1/2008 | Kapit et al. | |
| 2008/0052126 A1 * | 2/2008 | Sasai et al. | 705/3 |
| 2010/0076780 A1 | 3/2010 | Mahesh et al. | |
| 2010/0145720 A1 * | 6/2010 | Reiner | 705/2 |
| 2010/0256991 A1 * | 10/2010 | Ishikawa | G06F 19/321 |
| | | | 705/3 |
| 2010/0306218 A1 * | 12/2010 | Bacon | 707/759 |
| 2014/0149407 A1 | 5/2014 | Yuechen et al. | |

\* cited by examiner

230

Bi-Rads

Tabs: MRI, Pathology, Ultrasound, Findings

- Lateralty
- Depth
- Location

Sub-tabs: Mass, Additional Information

- Shape
- Orientation
- Margin
- Lesion Boundry
- Echo Pattern
- Posterior acoustic features
- Surrounding Tissue

Measurements

[Add] [Clear]

FIG. 2B

TITLE:
MAM BILATERAL (DIAGNOSTIC) & MAM BREAST ULTRASOUND.

CLINICAL HISTORY:
History of benign left breast biopsy. No current breast complaints.

FINDINGS:
Three standard views of each breasts were performed. As well, multiple spot compression views were performed of the left breast using both digital and analog technique. Spot compression views of the right breast were obtained. Bilateral breast ultrasound was performed. There is redemonstration of heterogeneously dense fibroglandular tissue. A linear marker was placed on a scar overlying the left breast. There is an area of architectural distortion at the 12 o'clock position of the left breast at site of prior biopsy. This has been stable since 1999. There is a new 5 mm spiculated mass within the left breast at approximately the 3 o'clock position. A new 1.4 cm nodular density has developed within the left upper outer quadrant. Multiple calcifications within each breast are unchanged. Benign appearing lymph nodes are projected over the axilla. Bilateral breast ultrasound was performed. At the 10 o'clock position of the right breast, two contiguous cysts are present measuring in aggregate 1.1 cm x 4.0 mm. This corresponds to the circumscribed nodular density seen in the right upper outer quadrant. Extensive ultrasound imaging of the left breast fails to demonstrate a discrete cystic or solid lesion. Therefore, digital mammogram of the left breast was performed using roll technique in the CC and LM projections. Persistent 5 mm spiculated density is present in the left upper outer quadrant.

IMPRESSION:

REPORT VIEWER USING RADIOLOGICAL DESCRIPTORS

The present system relates generally to a report viewer and, more particularly, to a smart report viewer for viewing reports using a predetermined set of radiological descriptors, such as descriptors used in BIRADS (Breast Imaging Reporting and Data System), referred to as BIRADS descriptors used in medical imaging systems, and a method of operation thereof.

Physicians (e.g. radiologists and oncologists) are dealing with increasing amount of information to diagnose and treat patients optimally. Patients with cancers, for instance, frequently undergo imaging examinations, and over time they have tens of studies in their medical records. After imaging a breast, for example, using a mammogram or ultrasound, a radiologist looks at the image(s) and writes a report providing an opinion on the health of the breast shown in the image(s) using current images and prior reports, images or examinations (exam) which are compared with the current images. That is, each time physicians read a new examination (exam), they need to compare the current exam with prior ones in order to determine the progress of previously identified lesions and discover new lesions if any. This task requires physicians to read, interpret, and correlate findings in both images and/or reports, including comparing current and prior images and/or reports, which is both workflow-wise time-consuming and clinically challenging.

Solutions have been proposed to help physicians to perform such tasks easily. The American College of Radiologists has set up standards for rating images using, e.g., mammograms, which is called BIRADS. BIRADS is designed to document breast cancer studies in a structured manner using standardized vocabulary. Systems have been developed to prepare radiology reports of breast cancer patients using BIRADS.

BIRADS is designed to document breast cancer studies in a structured manner using standardized vocabulary. The Integral Breast™ product of Philips Healthcare™ allows radiologists to annotate lesions according BIRADS on images and stores the annotation in databases. The next time when radiologists read studies of recurring patients, they can view prior images with annotated findings without reading through the associated text reports. This significantly saves on reading time.

FIG. 1 shows a report 100 using BIRADS for annotating images that includes various sections, such as Patient Information section 110, Study Overview section 120, Overall Conclusion section 130, and 'Finding 1 Details' section 140 that includes BIRADS finding and descriptors, such as selected from menus and/or lists of a GUI 160 shown at the right side of FIG. 1. The Patient Information section 110 includes patient identifying and other relevant information, such as the name and ID number assigned to the patient; sex, date of birth and relevant history of the patient; and report requester. The Study Overview section 120 shows diagrams 122 of front and side views of the right and left breasts of the patient with any detected lesions, as well as the name of the physician or radiologist, study date and other scan information shown in boxes 124 above the diagrams 122, and other data and finding in a box 126 below the diagrams 122, such as breast density noted as being extremely dense.

The Overall Conclusion section 130 includes notes and recommendations, where three box entries are show, for example, where the first box 132 includes "large mass detected in right breast. In addition, several calcifications are present in both breasts." The second box 134 includes an "Overall BI-RADS assessment category" indicated as "4A", where BI-RADS category 4 indicates 'Possibly Malignant,' 'Suspicious Abnormality,' and/or 'Not characteristic of breast cancer, but reasonable probability of being malignant; biopsy should be considered,' for example. The third box 136 of the Overall Conclusion section 130 shown in FIG. 1 may indicate 'Follow-up recommendation: Targeted US (Ultra Sound), if negative then Follow-UP MRI."

The Finding 1 Details section 140 include box 142 with Finding type and Mass information, such as BIRADS assessment category 4A indicating 'Low Suspicion.' Below box 142 the breast diagrams 122 are shown again that also include added annotation(s) 144. A 'Location' box 146 is located below the diagrams 122 and includes location identifying information of any mass or lesion identified in the diagrams 122, such as, Laterality=Right; O'clock position or region=5 o'clock; Depth=Anterior. The next box below the 'Location' box 146 is entitled 'Mass Properties' and includes BIRADS descriptions of the mass or lesion identified in the diagrams 122, such as Shape=Lobular; Margin=Obscured; Density Modifier=High density. Further boxes may also be included, such as box 150 entitled 'Associated Finding' with categories such as 'Skin retraction', 'Post-surgical scar,' etc. Further, key radiological images may be shown, such as x-ray mammogram images 170.

To use such systems optimally, legacy studies need to be annotated in the same manner. Legacy studies are studies that were diagnosed and documented as free or unstructured text reports, before the introduction of systems like BIRADS. In practice, legacy studies are not usually "re-annotated" due to quality-compliancy issues, cost and lack of resource.

However, physicians need to review prior studies or reports and compare them with current studies/reports. Manually comparing prior and current studies is time consuming and prone to possible errors in noting or missing to note certain information needed for proper comparison and diagnosis.

To truly benefit from using systems like BIRADS, physicians need to efficiently read and use legacy unstructured free text reports and structured BIRADS findings at the same time. This calls for a method that mediates between the "new" structured data, where descriptors or findings are selected from a limited or predefined set of descriptors or findings, and the "old" plain text reports, also referred to as free-text reports or unstructured-text reports, where any words, descriptors or findings may be used without any restrictions, i.e., without being limited to any particular or predefined set of words, descriptors or findings. Accordingly, there is a need for physicians to efficiently read and use legacy unstructured free text reports and structured BIRADS findings at the same time. Further, there is a need to mediate between the "new" structured data of BIRADS, for example, and the "old" plain text reports.

One object of the present systems, methods, apparatuses, and devices (hereinafter system unless context indicates otherwise) is to overcome the disadvantages of conventional systems and devices, including aiding the preparation of a proper study/report and diagnosis that takes into account relevant prior studies, e.g., for comparison with current studies, such as by suggesting prior studies that are relevant to the selected BIRADS annotation and by highlighting fragments of sentences, or groups of sentences, relevant to the selected BIRADS annotation.

Illustrative embodiments include a method, and a report viewer comprising a processor for performing the method and/or various engines and modules, for viewing a structured report, such as medical report describing radiological images using descriptors selected from a predefined list of descriptors, such as BIRADS descriptors, comprises the acts of opening the medical report; and in response to the opening act, searching by a processor for a further report related to the descriptors of the medical report, and highlighting words and/or sentences in the further report that match keywords derived from the descriptors. The medical report and the further report may be displayed simultaneously with the words and/or sentences being highlighted. The further report may be selected from a plurality of reports found by the search. In addition, the further report comprises an unstructured text report, and the method further comprises mapping the descriptors to findings in the text report and highlighting the findings.

The opening act may include the act of selecting the descriptors by a user, where the searching and highlighting acts are performed in response to the selecting act. Further, the descriptors may be automatically extracted from the first report in response to the opening act. The medical report may include an image annotated with the descriptors, and the descriptors may be automatically extracted from the image in response to the opening act.

The searching may include analyzing by a report analyzer the further report to obtain interpretations; translating by an ontology engine the descriptors into the keywords; and matching by a reasoning and matching engine the keywords with the interpretations to identify interpretations that match with the keywords. Further, the analyzing may includes segmenting the further report into sections; identifying sentences in the sections; grouping words in the sentences to form grouped words for each sentence; determining modality and laterality of the each sentence from the grouped words; and mapping the modality and laterality of the each sentence to modality and laterality words to obtain the interpretations.

Translating by the ontology engine, for example, may include parsing the descriptors to obtain list of properties corresponding to the descriptors; associating each property with semantically relevant words using a mapper that accesses an ontology database; and stemming the semantically relevant words to obtain the keywords.

A further embodiment includes a computer program product including non-transitory computer data stored on a tangible computer readable medium, where the computer program product comprised program code configured to perform the one or more the acts in accordance with the methods for viewing a report generated and/or annotated using a limited or predefined set of descriptors, such as BIRADS descriptors.

These and other features, aspects, and advantages of the apparatus, systems and methods of the present invention will become better understood from the following description, appended claims, and accompanying drawings where:

FIG. 2B shows a BIRADS GUI shown in FIG. 2A in greater detail;

FIG. 6 shows an illustrative example of a highlighted unstructured report where relevant portions are highlighted according to one embodiment of the present system;

FIG. 9 shows an illustrative graphical user interface according to one embodiment of the present system.

Figure 1:
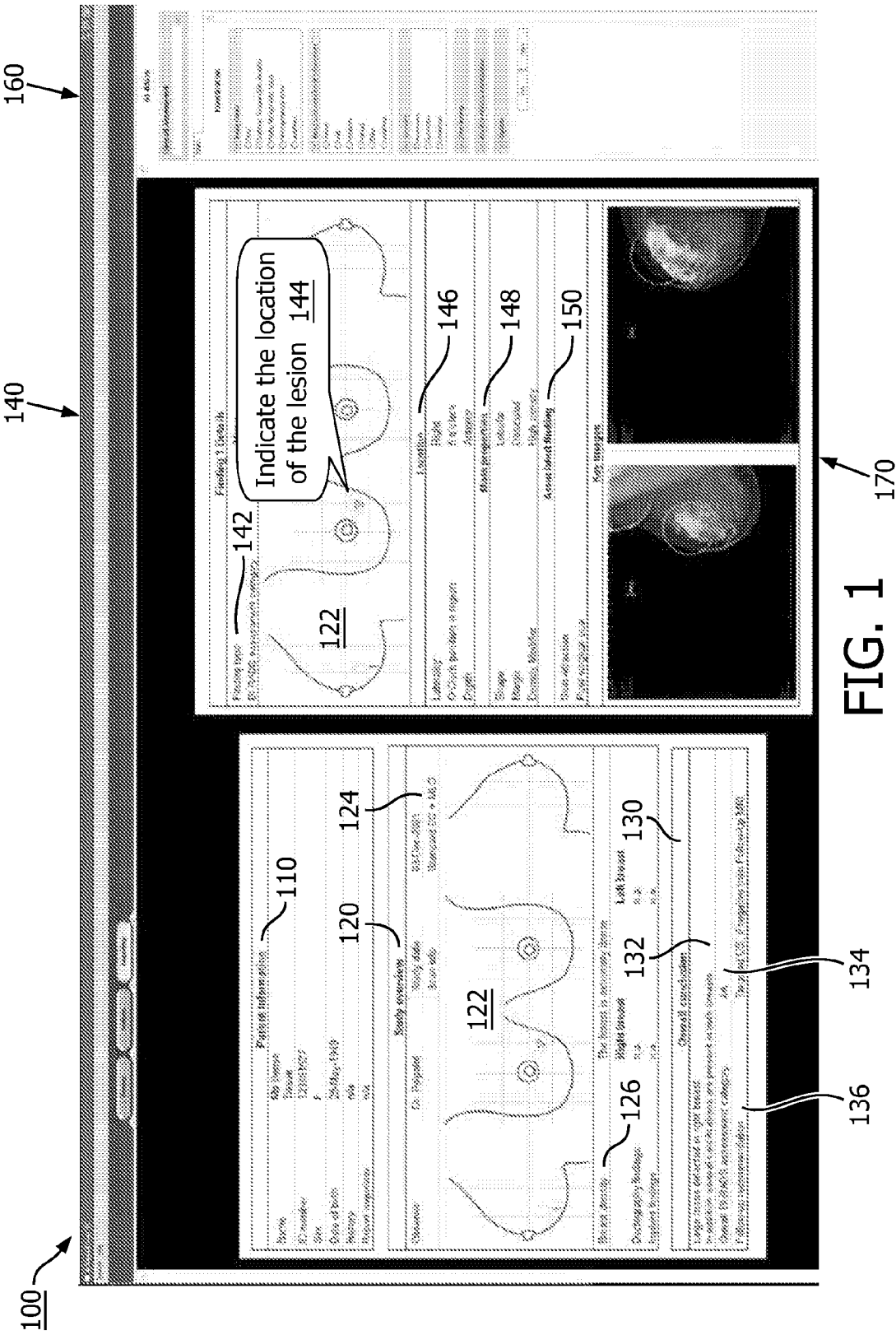
FIG. 1 shows a conventional report using structured BIRADS data for annotating images.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques and methods are omitted so as not to obscure the description of the present system. It should be expressly understood that the drawings are included for illustrative purposes and do not represent the scope of the present system. In the accompanying drawings, like reference numbers in different drawings may designate similar elements.

For purposes of simplifying a description of the present system, the terms "operatively coupled", "coupled" and formatives thereof as utilized herein refer to a connection between devices and/or portions thereof that enables operation in accordance with the present system. For example, an operative coupling may include one or more couplings of a wired connection and/or a wireless connection between two or more devices that enables one and/or two-way communication paths between and among the devices and/or portions thereof. For example, an operative coupling may include a wired and/or wireless coupling to enable communication among a processor, memory, server and other devices, such as parser, segmenters, mappers and/or stemmers.

The term rendering and formatives thereof as utilized herein refer to providing content, such as digital media which may include, for example, images annotated with descriptors, list of descriptors for selection and annotation of desired portions of images, etc., such that it may be perceived by at least one user sense, such as a sense of sight and/or a sense of hearing. For example, the present system may render a user interface on a display device so that it may be seen and interacted with by a user. Further, the present system may render audio visual content on both of a device that renders audible output (e.g., a speaker, such as a loudspeaker) and a device that renders visual output (e.g., a display). To simplify the following discussion, the term content and formatives thereof will be utilized and should be understood to include audio content, visual content, audio visual content, textual content and/or other content types, unless a particular content type is specifically intended, as may be readily appreciated.

The user interaction with and manipulation of the computer environment may be achieved using any of a variety of types of human-processor interface devices that are operationally coupled to a processor or processors controlling the displayed environment. A common interface device for a user interface (UI), such as a graphical user interface (GUI) is a mouse, trackball, keyboard, touch-sensitive display, a pointing device (e.g., a pen), etc. For example, a mouse may be moved by a user in a planar workspace to move a visual object, such as a cursor, depicted on a two-dimensional display surface in a direct mapping between the position of the user manipulation and the depicted position of the cursor. This is typically known as position control, where the motion of the depicted object directly correlates to motion of the user manipulation.

An example of such a GUI in accordance with embodiments of the present system is a GUI that may be provided by a computer program that may be user invoked, such as to enable a user to select and/or classify/annotate content such as, for example, an image annotated with descriptors or a textual content with highlighted portions.

Figure 2A:
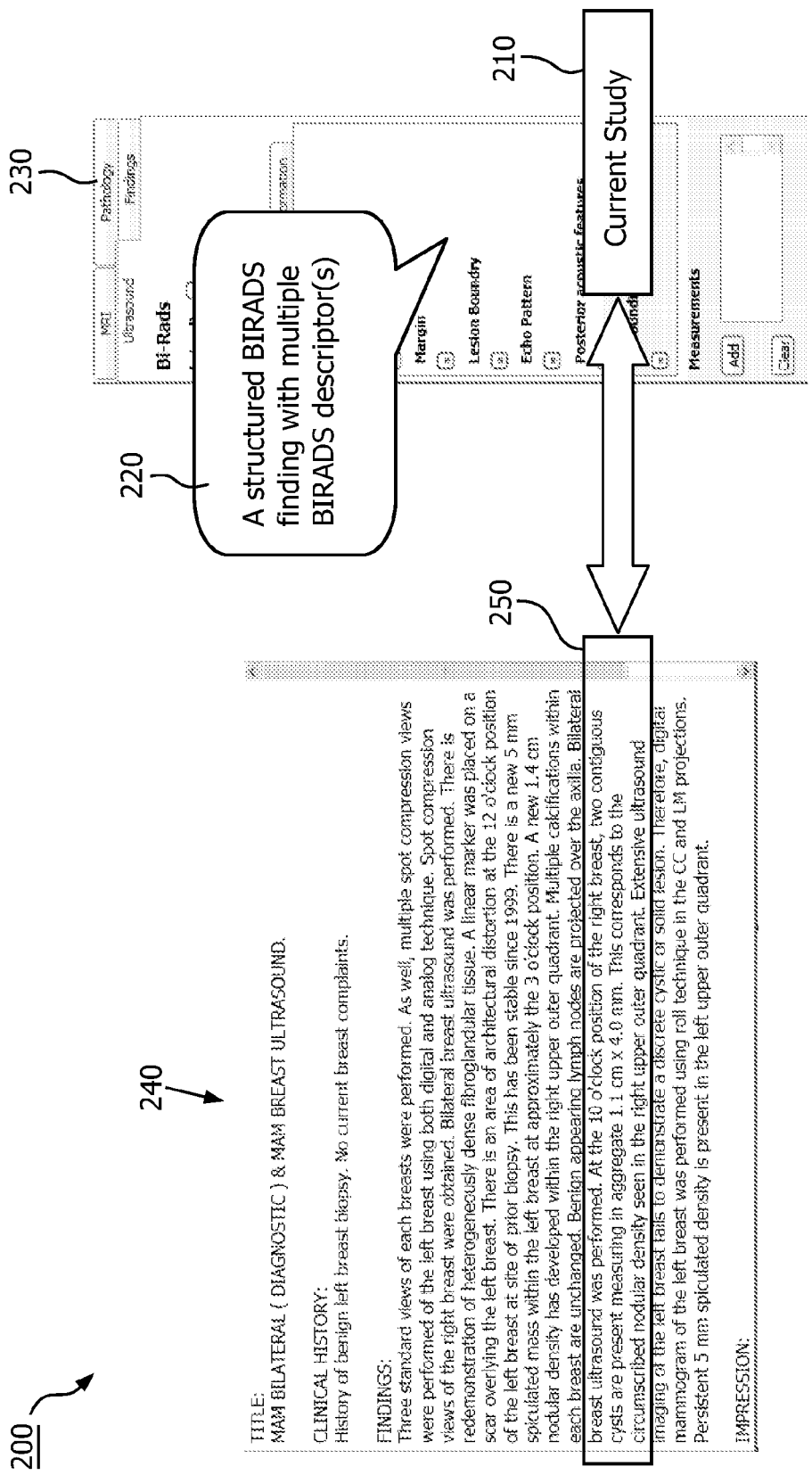
FIG. 2A shows views of reports that are automatically correlated and concurrently displayed according to one embodiment of the present system.

FIG. 2A shows a view 200 of reports that are automatically correlated and concurrently displayed according to one embodiment of the present systems and methods. As shown in FIG. 2A, in one current study 210 (also referred to as a reference study) shown on the right side of FIG. 2A, a lesion in an image is or was described using BIRADS descriptors 220 selected from a BIRADS GUI 230, where images may by annotated with BIRADS descriptors 220 using systems like Integral Breast™, or other systems, such as described in a publication entitled "Complete Digital Iconic and Textual Annotation for Mammography" by Wittenberg, et al., available on the world wide web at sunsite.informatik.rwth-aachen.de/Publications/CEUR-WS/Vol-283/p091.pdf, which is incorporated herein by reference in its entirety, and is published in CEUR Workshop Proceedings, March 2007, Munich, volume 283, book title "Bildverarbeitung fur die Medizin," pages 91-95. FIG. 2B shows the BIRADS GUI 230 by itself for better clarity.

The current or reference study 210 may be any desired or selected study including a BIRADS study, where descriptors are selected from a limited or predefined/predetermined set of descriptors. For simplicity, the reference study 210 will be referred to as the BIRADS study, but it should be understood that the reference study 210 may be any desired and/or selected study to be compared to different related and/or selected studies, referred to herein as prior studies. On the left side of FIG. 2A, a text report 240 of one prior study in a legacy system using unstructured or free/plain text is shown, where there are no restrictions on any descriptors or words, and may be dictated by a radiologist reviewing images for example. FIG. 6 shows the text report 240 by itself for better clarity, where instead of the text that matches BIRADS descriptors being surrounded by a box, the matched text is highlighted.

The prior study may not necessarily predate the current or reference study 210 and may be any study, such as a study with free or unstructured text. The present system automatically find the prior study 240 that is relevant to the current study 210, and correlate portions of the prior study 240 that match the BIRADS descriptors to the BIRADS descriptors selected from the BIRADS GUI 230 and/or to the current study/images that include annotated BIRADS descriptors. For example, the present system automatically finds a list of prior studies related to breast examination of the same patient of a current breast study, ordered by any desired or selected order, such as by date. The search or automatic extraction may be narrowed to include attributes, such a modality and/or laterality, which may be user selected or automatically extracted from the BIRADS descriptors. For example, when the modality is 'ultrasound' (US) and laterality is 'right,' then prior art reports that include US and right breast information (e.g., text and/or images) for the particular patient are automatically extracted, e.g., using text and/or image recognition devices or algorithms, where the latest report of such reports may be deemed to be the most relevant prior report. Alternatively, or in addition, the prior study 240 may be user selected for correlation and highlighting of relevant words, sentences and/or groups of words and sentences that are related to or that match the BIRADS descriptors that may be user selected or automatically extracted from an image that is annotated with the BIRADS descriptors. It is also understood than the present system can also be used to compare studies of other patients with the current study.

Depending on the modality of the current study including annotations, e.g., BIRADS annotations, of a lesion on an image describing the lesion where such BIRADS annotations may be superimposed on the image, physicians need to know which prior studies reports have the same modality as that of the current annotation/study. In case of breast cancers, mammography using x-rays (MAM), ultrasound imaging (US), and magnetic resonance imaging (MRI) are modalities that are often used. Next, physicians need to open up reports of those prior studies including the same modality and read the content of the reports. Often reports contain findings of multiple modalities. In case of breast cancer reports, mammography and ultrasound findings may be reported in the same document. Physicians need to find sentences where the annotated lesion, annotated using the current study, e.g., using BIRADS, was described in the prior study with the same modality. That is, if the current modality is US or ultrasound, and a prior report includes both MAM and US related text, then physicians need to find text related to US, and not to MAM. After finding prior reports related to the currently annotated lesion, physicians will compare the progression of the lesion, in terms of size, shape, margin, density etc.

As can be readily ascertained, performing such a task manually is time-consuming and prone to errors. The present systems and methods help physicians to perform the above-mentioned tasks by finding suggesting prior studies that are relevant to the selected BIRADS annotation, and by highlighting fragments of sentences relevant to the selected BIRADS annotation. Thus, in the prior example, if the current report or study is a US study of a right breast of a patient, then prior relevant reports are found and suggested, where such prior reports are deemed relevant if they include studies or text related to US studies of the right breast of the patient. In the case where a relevant prior report includes studies of both the right and left breasts of the patient, using both US and MAM modalities, than only portions of the prior report that are relevant to the current study are highlighted, namely, portions that are related US of the right breast. Thus, portions in the prior study related to the left breast, or related to MAM of the right breast are not highlighted, since these portions are not relevant to the current study which is for an US study of the right breast of the patient.

Individually reading through a collection of text reports to identify sentences relevant to the selected annotation (e.g., US, right breast of patient X) is challenging. To assist physicians in identifying relevant sentences, the present systems and methods automatically searches, suggests and/ or provides related prior studies, such as the prior study 240 with the free or plain/unstructured text report shown on the right side of FIG. 2A, as well as automatically highlight sentences that are related to the annotation, e.g., BIRADS annotation, of the current study 210 shown on the right side of FIG. 2A. In this embodiment, the relevant sentences of the selected prior study 230 are highlighted by surrounding the relevant sentences with a box(s) 250, for example. It should be understood that highlighting can includes at least one of changing the appearance of selected report content such as word(s) and/or sentence(s), to be different from other report portions, or painting and/or superimposing a colored background on the selected report or content portion(s), or surrounding the selected portion(s) of the content by a border(s) or box(es), or any combination(s) thereof.

In addition to automatic selection of the relevant prior study 230, the present system may select any desired study for comparison with a current or reference study, such as the study 210 annotated in BIRADS, also referred to as the BIRADS study 210. The present system may include a processor or controller configured to present an interface, such as displaying a graphical user interface (GUI) on a display or monitor with a menu including a list of prior study for user selection. The presented list of prior studies may be ordered by a selected criteria(s), such as date, examination type, modality, and/or relevance, or importance, as indicated in the prior study or indicated in metadata associated in the prior study.

Keyword-based highlighting of documents can be found in many existing applications. Using Internet Explorer, for example, the user can search keywords in a web page and the application can highlight all occurrences of the keywords. Instead of highlighting all occurrences of keywords, the present system maps or translates selected BIRADS description of lesions to syntactically, semantically, and clinically relevant words that then are used to determine and highlight relevant sentences and/or portions or groups of the relevant words that are determined to be more related to selected BIRADS descriptions or BIRADS annotations added to an image. For example, if the image is that of the right breast, than all occurrences of 'breast' in free-form or unstructured text will not be highlighted. Rather, the highlighting is limited to 'breast' associated with the right breast, where occurrences of 'breast' associated with the left breast will not be highlighted. Thus, the present system associated a first descriptor with at least one other descriptor of the current report to determined and highlight relevant words or sentences in the prior report. For example, 'breast' may be associated with 'right' or (laterality, right), so that all occurrences of breast are not highlighted in the prior report, and only occurrences of breast associated with the 'right breast' are highlighted. Further descriptors may be associated with the first descriptors or 'breast' such as ultrasound or (modality, US), and thus, only occurrences of breast associated with the 'right breast' and ultrasound or US are highlighted, and occurrences in the prior report of 'right breast' and ultrasound or x-ray mammogram or MAM are not highlighted. Furthermore, it is often the case that the radiologist will only explicitly mention the location (e.g., "right breast") of the lesion in the beginning sentence and will not repeat the location information in following sentences. The present system designates that the following sentences relate to the same lesion, and thus should be highlighted as well, as described in the present system.

Figure 3:
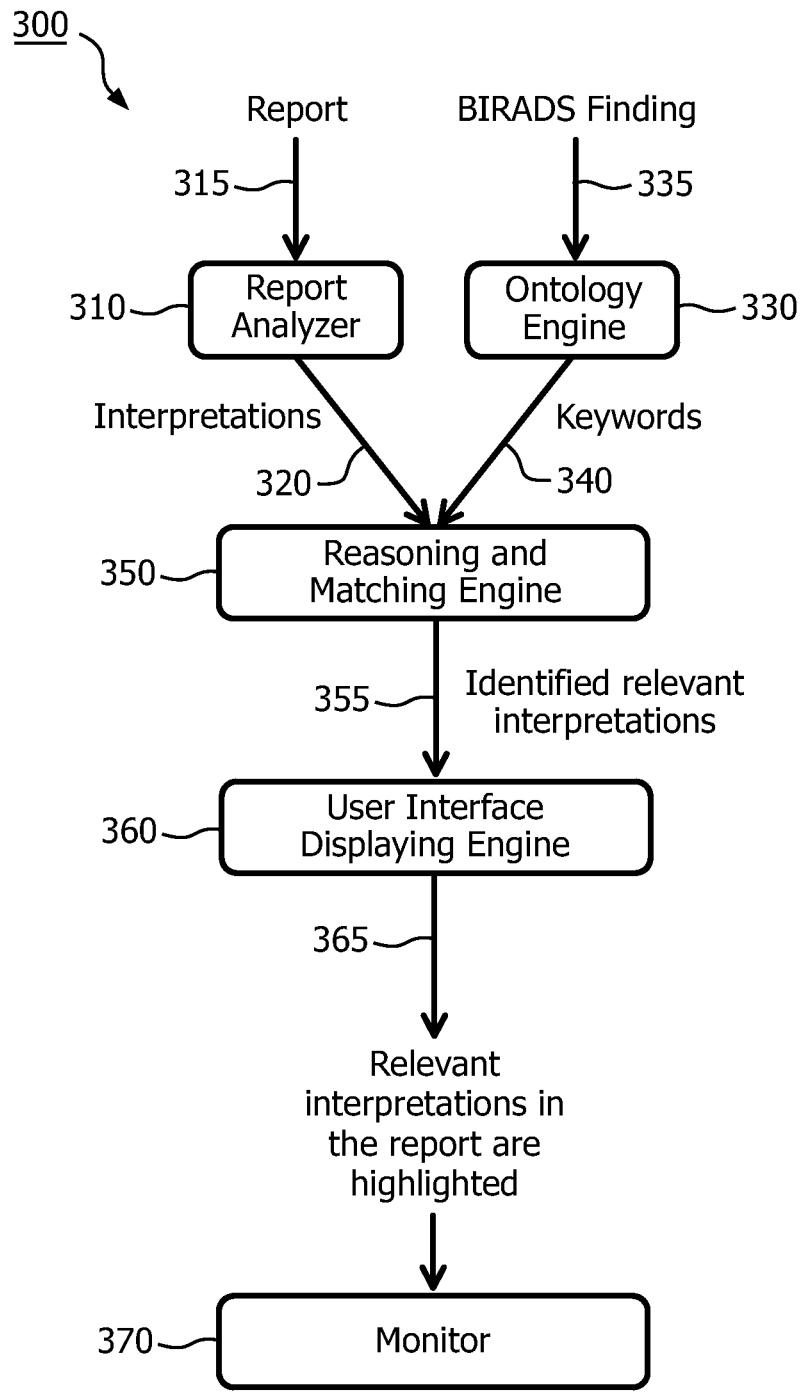
FIG. 3 shows a block diagram illustrating a system with interaction flow between components in accordance with one embodiments of the present system.

FIG. 3 shows a block diagram illustrating a system 300 with interaction flow between system components that are operationally coupled to each other in accordance with embodiments of the present system. As shown in FIG. 3, the system includes report analyzer 310, which may be a semantic natural language processing module that receives and turns an unstructured radiology report 315 into a collection of interpretations 320 for output. Each interpretation 320 is associated with a modality attribute that indicates the type of the image study (e.g., X-ray such as a mammogram, ultrasound, MRI and other image types,) from which a finding was identified, where the finding may be given BIRADS descriptors and referred to as a BIRADS finding that may be automatically found from the studied image or provided by a radiologist reading the image, for example. Each interpretation 320 has attributes that describe, if any, various aspects of a lesion, e.g. laterality, locality, depth, shape, and/or other attributes, such as shown in the BIRADS ultrasound GUI 230 in FIG. 2B, for example.

The system 300 further includes an ontology engine 330 that receives descriptors or finding 335 that describe image content, e.g., a lesion in the image of a breast, such as BIRADS descriptors that are automatically generated from automatic machine analysis of the image and/or provided by a radiologist reading the image. The ontology engine 330 translates at least one BIRADS descriptor into a list of syntactically and semantically related keywords 340. For example, a BIRADS descriptor such as "Laterality" is translated into lateral, side, edge, border, right, R, left, L, and other synonyms and abbreviation.

As shown in FIG. 3, the system 300 further includes a reasoning and matching engine 350 operationally coupled to the report analyzer 310 and the ontology engine 330. The reasoning and matching engine 350 translates a BIRADS finding, which may be a set of grouped BIRADS descriptors, to a set of search cues, and matches the search cues with the interpretations 320 provided from the report analyzer 310 to determine or identify matched or relevant interpretations 355.

For example, an Ultrasound (US) BIRADS finding may include descriptors like (modality, US), (Laterality, Right), (Location, 10 o'clock). "US" is semantically mapped to words like "ultrasound", "echo", "echoic"; "right" to "right breast", "right side", "left axilla"; "10 o'clock" to "upper quadrant" and "upper inner quadrant". An interpretation of the second sentence in the following excerpt: "Bilateral breast ultrasound was performed. At the 10 o'clock position of the right breast, two contiguous cysts are present measuring in aggregate 1.1 cm by 4.0 mm . . . ," may include (modality, US) and (laterality, right). These interpretation, namely, (modality, US) and (laterality, right), match the modality, laterality and location descriptors of the ultrasound BIRADS findings and, therefore, the excerpt and/or the second sentence of the excerpt is highlighted.

The reasoning and matching engine 350 is further operationally coupled to a user interface displaying engine 360. In particular, the reasoning and matching engine 350 outputs the matched or identified relevant interpretations 355 to the user interface displaying engine 360. The user interface displaying engine 360 provides its output 365 to a monitor 370 to display the report 315 with relevant (or matched) fragments of the report being highlighted in accordance with the identified relevant interpretations 355 that match the BIRADS finding as determined by the reasoning and matching engine 350. A shown in FIG. 2 and FIG. 9, the highlighted prior report 240, 940 with free or unstructured text is displayed side by side with the BIRADS descriptors (e.g., 950, 960 in FIG. 9) associated with the highlighted portions of the prior or unstructured report. The BIRADS descriptors shown concurrently or simultaneously with the highlighted portions of the prior or unstructured report may be displayed as added annotations added to the image described by the BIRADS descriptors and/or BIRADS findings.

Figure 4:
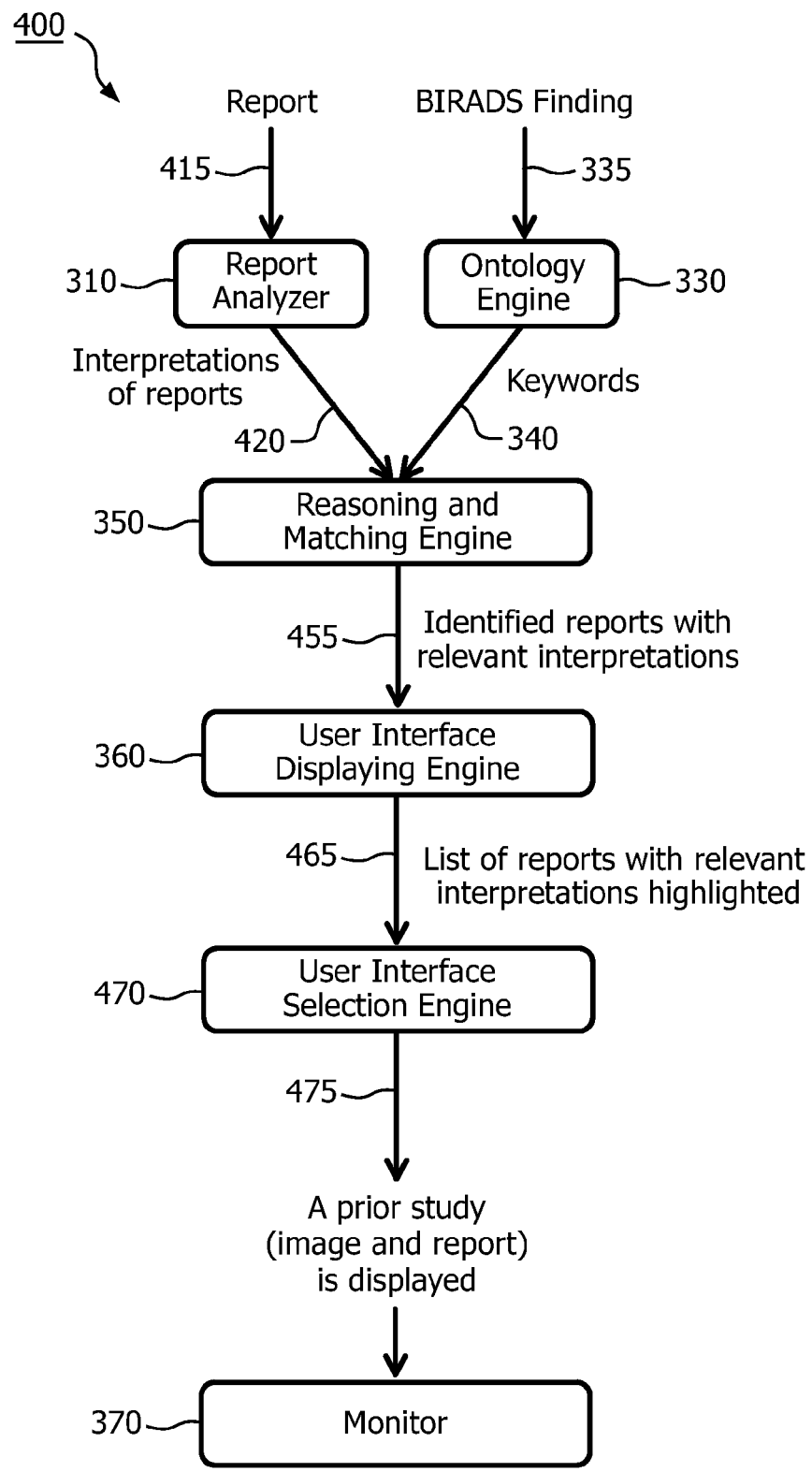
FIG. 4 shows a block diagram illustrating a system with interaction flow between components in accordance with another embodiment of the present system.

FIG. 4 shows a further system 400 which is similar to the system 300 shown in FIG. 3, except that the system 400 of FIG. 4 includes searching, finding and identifying multiple free-text or unstructured text reports 415, where the report analyzer 310 outputs interpretations 420 of the multiple reports 415, and where the system 400 of FIG. 4 further analyzes the interpretations 420 and keywords 340 to find or identify relevant reports and interpretations 455 by the reasoning and matching engine 350 that match the BIRADS finding. In this embodiment, the output 465 of the user interface displaying engine 360 includes a list of reports with the relevant interpretations highlighted. This output 465 with the list of reports is provided to a user interface selection engine 470 for user selection from among the list or report. Upon user selection of a report, the selected report 475 is displayed on the monitor 370.

Figure 5:
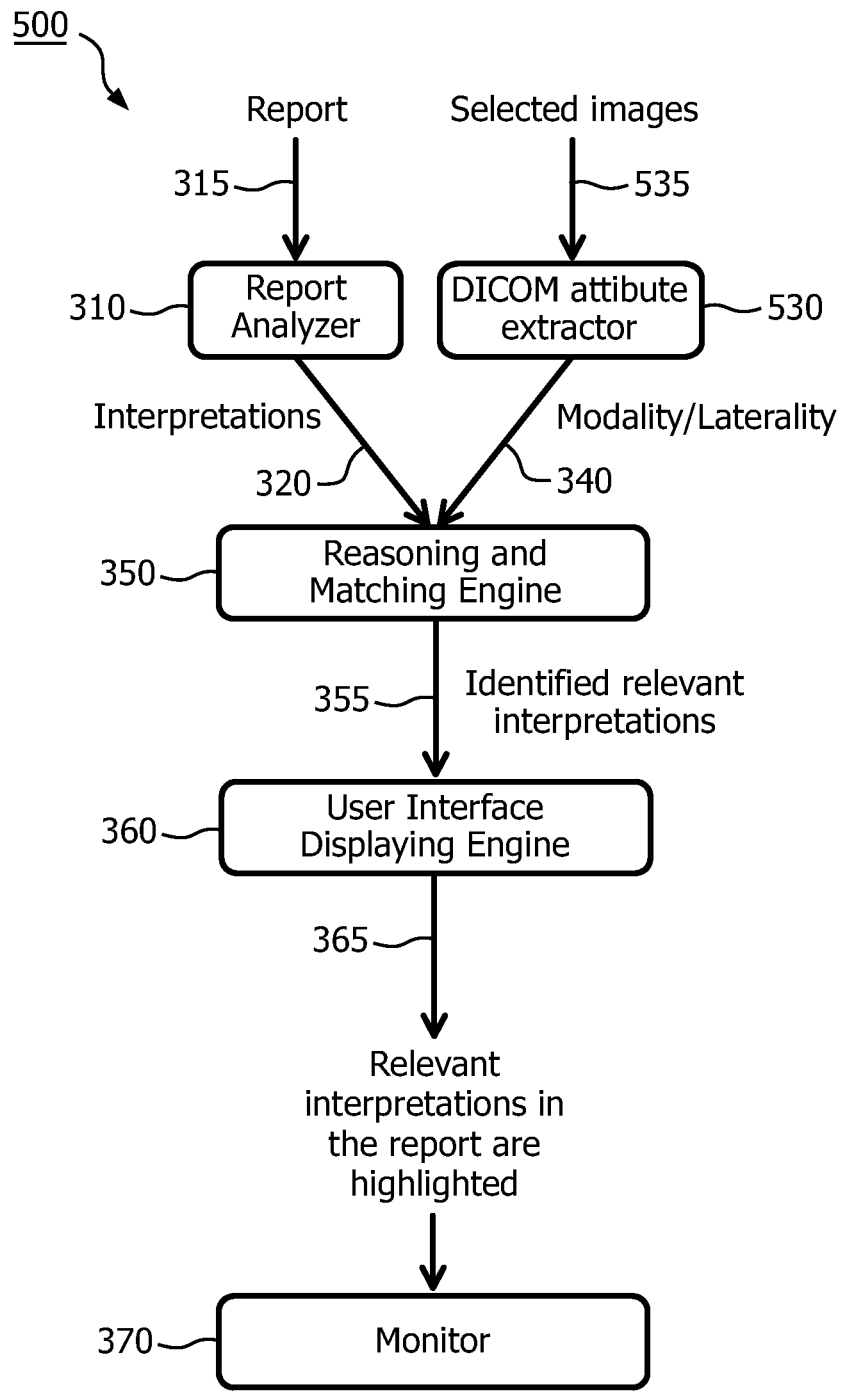
FIG. 5 shows a block diagram illustrating a system with interaction flow between components in accordance with a further embodiment of the present system.

FIG. 5 shows another system 500 where descriptors or content attributes are automatically extracted from selected content, e.g., images, instead of being provided by the system user or radiologist, for example. In this illustrative embodiment, relevant sentences of one prior report are displayed according to the modality/laterality attributes of DICOM images, e.g., when BIRADS descriptors are not available. As is well known, the Digital Imaging and Communications in Medicine (DICOM) is an industry standard for distributing and viewing medical image and other medical information between computers, such as to enable digital communication between diagnostic and therapeutic equipment and systems from various manufacturers.

Content attributes of DICOM images, for example, may be extracted from the content itself and/or from metadata associated with the image file. For example, image attributes may be automatically extracted using computer image and/or text analyzers and identifiers using computer vision and/or identification and extraction algorithms, for example, to detect and identify lesions in an image of a breast. Alternatively or in addition, such algorithms and/or computer vision may be used to automatically extract attributes by detecting, recognizing and/or identifying annotations or texts added to the image.

FIG. 5 includes components similar to those shown in FIGS. 3-4. While FIG. 5 shows the report analyzer 310 receiving one report 315 and providing interpretations 320, similar to FIG. 3, it should be understood that the report analyzer 310 may receive and analyze several reports 415 to produce interpretations 420 of the plurality of reports 451, as described in connections with FIG. 4. As shown in FIG. 5, an attribute extractor such as a DICOM attribute extractor 530 is configured to extract attribute from selected DICOM files or images 535, such as from metadata or from the content itself, such as using image analysis methods including computer vision, for example.

The DICOM attribute extractor 530 extracts and provides attributes 340 to the reasoning and matching engine 350. For example, the extracted attributes or keywords 340 may be modality, laterality, and other attributes of the DICOM file or content of the DICOM file, such as description and location of lesions in an image of a breast included in the DICOM file. Similar to the system 300 of FIG. 3, the reasoning and matching engine 350 compares the interpretations 320 from the report analyzer 310 with the extracted attributes 340, and identifies relevant interpretations 355 (of the report 315) that matches the extracted attributes or keywords 340. The relevant or matched report interpretations 355 are provided to the user interface displaying engine 360 that highlights the relevant interpretations and provides the report 365 with the highlighted relevant interpretations to the monitor 370 for display.

FIG. 6 shows an illustrative example of a highlighted unstructured report 600, similar to the unstructured report 240 of FIG. 2A, where relevant portions that match the BIRADS descriptors/findings are highlighted (instead of being surrounded by the box 250 shown in FIG. 2A). In the example shown in FIG. 6, the BIRADS finding includes an ultrasound finding with a circumscribed lesion in right breast in the right upper outer quadrant. This embodiment of the present system highlights the sentences in the unstructured report 600 that are ultrasound-specific and highlight relevant keywords that match the BIRADS descriptors/findings. Notably, sentences describing mammographic findings are not highlighted; the lesion is semantically mapped to "nodular density" and highlighted; ultrasonic findings of the left breast are not highlighted.

Figure 7:
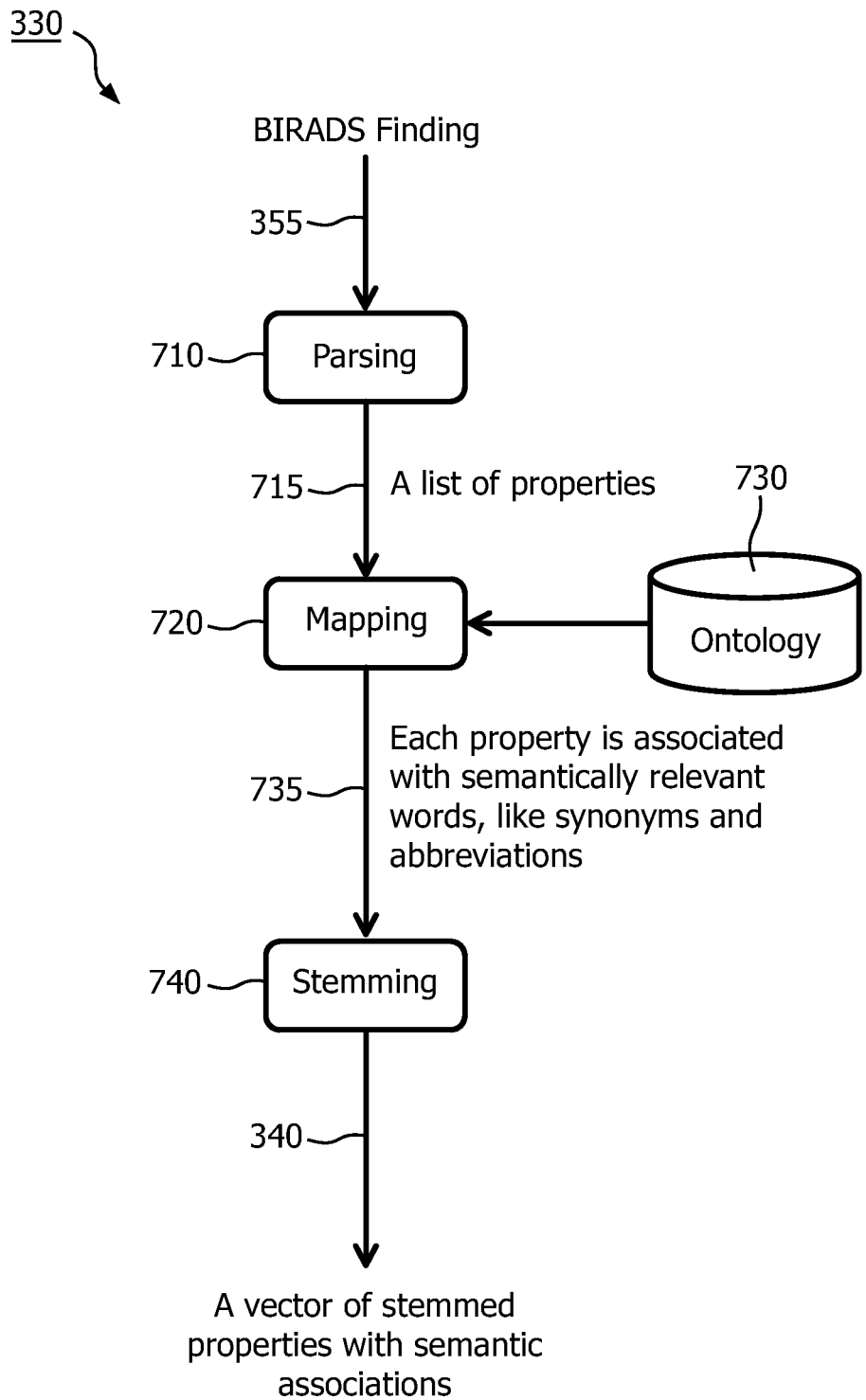
FIG. 7 shows an illustrative embodiment of an ontology engine shown in FIGS. 3-4 according to one embodiment of the present system.

FIG. 7 shows an illustrative embodiment of the ontology engine 330 shown in FIGS. 3-4. As shown in FIG. 7, the ontology engine 330 includes a parser or parsing module 710 that receives the BIRADS findings 335 and parses them into descriptors including text strings along with a list of properties 715 corresponding to the descriptors. Examples of properties are "Laterality: Left Breast", "Location: upper inner quadrant", "Shape: Irregular", "Margin: not circumscribed" and other BIRADS descriptors. The parsed BIRADS findings, descriptors or properties are provided to a mapper or mapping module 720 that accesses an ontology database 730, which may be an ontology server remotely located but operationally coupled to the mapper 720, or may be data stored in a local memory of the present system and operationally coupled to the mapper 720. The ontology database 730 includes words, synonyms and abbreviation and the like. The mapper 720 associates each property 715 of the BIRADS findings 335 with semantically relevant words 735 that match the property 715, including synonyms and/or abbreviation, for example. The relevant words 735 are stemmed by a stemmer to reduce the relevant words 735 to their stems, bases or roots, such as removing ending from the words to obtain root words. For example, the stemmer 740 identifies the root 'search' from words like 'searching' or 'searcher'. Other examples include stemming "heterogeneously" to obtain the stem "heterogeneous" and stemming "shadowing", which may be a value of the "posterior acoustic" property of an ultrasound finding, to obtain the stem "shadow." The stemmer 740 outputs stems also referred to as keywords 340, e.g., vectors of stemmed properties with semantic associations to the reasoning and matching engine 350 shown in FIGS. 3-4.

Figure 8:
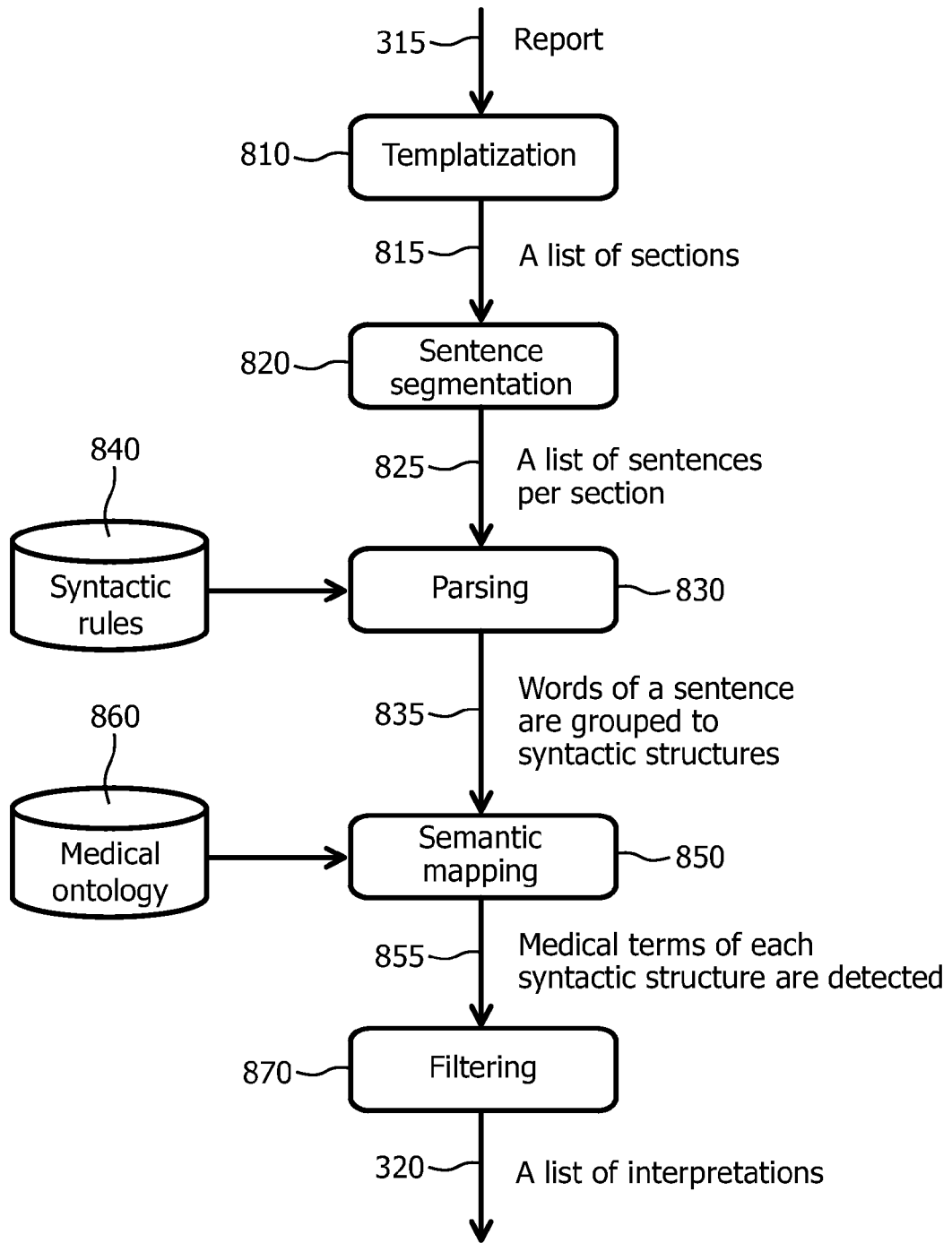
FIG. 8 shows an illustrative embodiment of a report analyzer shown in FIGS. 3-4 according to one embodiment of the present system.

FIG. 8 shows an illustrative embodiment of the report analyzer 310 shown in FIGS. 3-4. As shown in FIG. 8, the report analyzer 310 includes a templatization or segmentation module 810 that receives free-text or unstructured text reports 315 and segments the reports into segmented sections 815 (such as a header, history, procedure, findings and impressions), paragraphs and sentences. The segmented sections 815 are provided to a sentence segmentation module 820 that identifies sentences in the segmented sections 815. For each segmented sections 815, the sentence segmenter module 820 provides a list of sentences per section 825 to a parser or parsing module 830.

The parser 830 uses syntactic rules stored in a memory or database 840 for syntactic processing and parsing the received sentences 825 into words and sentences, and for grouping the words of a sentence to syntactic structures 835.

For example syntactic rules are used for describing the syntax of a given language such as English where, in accordance with the syntactic rules, where a processor is configured to parse, divide and/or separate a natural language sentence is into its constituent parts and/or categories, such as N, V, P categories, and the words of a sentence are assigned to the N, V, P categories. One example, of using a rule to group words and map the group to syntactic structures includes NVNP which describes that the sentence includes a noun phrase N, a verb V, another noun phrase N, and a preposition phrase P. Noun phrases are used in a semantic mapping 850, in which nouns are matched against a medical ontology 860, to determine whether the noun is a medical term or not, and to determine its semantic category (e.g., anatomy, disease, procedure, etc.)

The semantic mapping 850 determines the modalities of the report from the study's DICOM data that represents the image associated with the report, for example. If the infrastructure does not allow access to this data, then the modalities (e.g., MAM/US/MRI) can be determined or inferred from header information of the report. Typically the header includes the following: "R MAM BREAST ULTRASOUND", indicating the file or report includes both x-ray mammogram and ultrasound imaging information of the right breast, or "R MAM UNILAT DIGITAL DIAGNOSTIC" indicating a x-ray mammogram information of the right breast, for example.

A semantic mapping module 850 receives the syntactic structures 835 from the parser 830 and maps each modality to a selection of modality specific keywords that are used to discover starting points of discussions. A discussion includes consecutive sentences that are all related to a specific modality. The modality is assigned to all sentences of one discussion. In particular, the semantic mapping module 850 uses a medical ontology stored in a memory 860, which includes medical terms, to detect medical terms of each syntactic structure received from the parser 830 including mapping the modality to modality specific keywords.

The output 855 of the semantic mapping module 850 is operationally coupled to a filtering module 870 and includes detected medical terms of each syntactic structure. These detected medical terms 855 are filtered by the filtering module 870 to provide the list of interpretations 320 to the reasoning and matching engine 350 shown in FIGS. 3-4. The report analyzer 310 may also be referred to as a natural language processing module which is used to interpret sentences. Interpretations 320 are extracted that often include the problem detected from the image, body location, modifiers, etc. For example, Medical Language Extraction and Encoding System (MEDLEE) may be used to generate such interpretation. Furthermore, the modality keywords derived by the semantic mapping module 850 are assigned to the interpretations 320 by the natural language processing module or report analyzer 310.

Returning to FIG. 7, each BIRADS descriptor, typically a pair of text strings, included in the BIRADS finding 335 is translated into syntactically and semantically keywords using the ontology server 730. The property or descriptor name and value of a selected BIRADS descriptor are first stemmed by the stemmer 730. For example, a mammogram finding may include a list of descriptors. One description describes one aspect of the lesion. For example, "Laterality" may be the name of the descriptor, and its value may be "left", "right", "both", and "none". This descriptor (i.e., "Laterality") describes the side of breast the lesion resides in. Other often used descriptors include "Depth", "Location", and "Calcification characteristic" for example. Stems are used as the first class of keywords. For example, a conventional Porter Stemmer may be used. Next, the property name and values are semantically mapped by the mapping module 720.

As an illustrative example, the location of a lesion is typically characterized by the quadrant and clock position. Using the ontology engine 330, 9 to 12 o'clock positions of the left breast is mapped to the upper inner quadrant of the left breast and 9 to 12 o'clock positions of the right breast the upper outer quadrant of the right breast. Further, "mass" is mapped to "lesion", which is a more general concept using conventional Unified Medical Language System/Systematized Nomenclature of Medicine (UMLS/SNOMED™) ontology. All derived keywords are stemmed.

To summarize the following acts are performed to map a BIRADS-annotation to findings in text reports. The BIRADS-annotation may be provided or added to an image (e.g., of a breast) automatically or manually by a radiologist reading the image, for example.

1. Using the report analyzer or natural language processing module 310, reports 315 are segmented by the segmenter 820 into sections (header, history, procedure, findings and impressions), paragraphs and sentences. The modalities of the report 315 may be obtained from the study's DICOM data. If the IT infrastructure does not allow access to this data the modalities (MAM/US/MRI) is determined from header information of the report. Typically the header looks as follows: "R MAM BREAST ULTRASOUND", "R MAM UNILAT DIGITAL DIAGNOSTIC."

2. Each modality is mapped by the semantic mapping module 850 to a selection of modality specific keywords that are used to discover starting points of discussions, where s discussion includes consecutive sentences that are all related to a specific modality. The modality is assigned to all sentences of one discussion.

3. The natural language processing module 310 is used to interpret sentences. Interpretations are extracted that often includes descriptions of problem, body location, modifiers. MEDLEE in this case can be used to generate such interpretation. Furthermore, derived modality information in step 2 is assigned to interpretation.

4. Each BIRADS descriptor, typically a pair of text strings, is translated into syntactically and semantically keywords using the ontology server 330. BIRADS finding and/or descriptors are parsed by the parser 710 to obtain a list of properties of the BIRADS descriptors. The name and values of each property are semantically mapped such as by the mapper 720 to obtain semantically relevant words such as synonyms and/or abbreviation associated with each property. The property name and value of a selected BIRADS descriptor are then stemmed by the stemmer 740. Stems are used as the first class of keywords. Porter Stemmer may be used here for example. If desired, multiple mapping and/or stemming may be performed where, for example, the property name and value of a selected BIRADS descriptor are first semantically mapped by a mapper to find relevant words, and then the words are stemmed by a stemmer. Next, the found or determined relevant words or semantic associations are stemmed to obtain a vector(s) of stemmed properties with stemmed semantic association.

a. The location of a lesion is typically characterized by the quadrant and clock position. Using the ontology engine, 9 to 12 o'clock positions of the left breast is mapped to the upper inner quadrant of the left breast and 9 to 12 o'clock positions of the right breast the upper outer quadrant of the right breast.

b. "Mass" is mapped to "lesion", a more general concept using, for example, UMLS/SNOMED ontology.

c. All derived keywords are stemmed.

5. When the user selects a BIRADS finding which can comprise a multiple of BIRADS descriptors, the system evaluates a numeric relevance score indicating how well each sentence of each discussion matches the selected BIRADS finding.

a. One straightforward way is to compute the number of occurrences of stems derived in Step 4 in a sentence. The more the number is, the more relevant the sentence is.

b. A clinically more relevant approach is to match a sentence to a BIRADS finding according to interpretations. In this approach, an interpretation is treated as a feature vector in the same BIRADS space as a BIRADS finding. For example, the interpretation of a sentence can be modeled as a vector of properties including modality, laterality, location, margin and so on, in the same way as a BIRADS finding. To compute the numeric relevance score of a sentence with respect to a BIRADS finding, a property in the vector of the interpretation is matched to that of the BIRADS finding: if the values of property is the same, the matching score of this property is 1; otherwise 0. Furthermore, a weight is assigned to the property: the more important the property is for the current clinical context, the higher the weight is. The relevance score of a sentence with respect to a BIRADS finding is the sum of the multiplication of the weight and matching score of properties.

Figure 9:
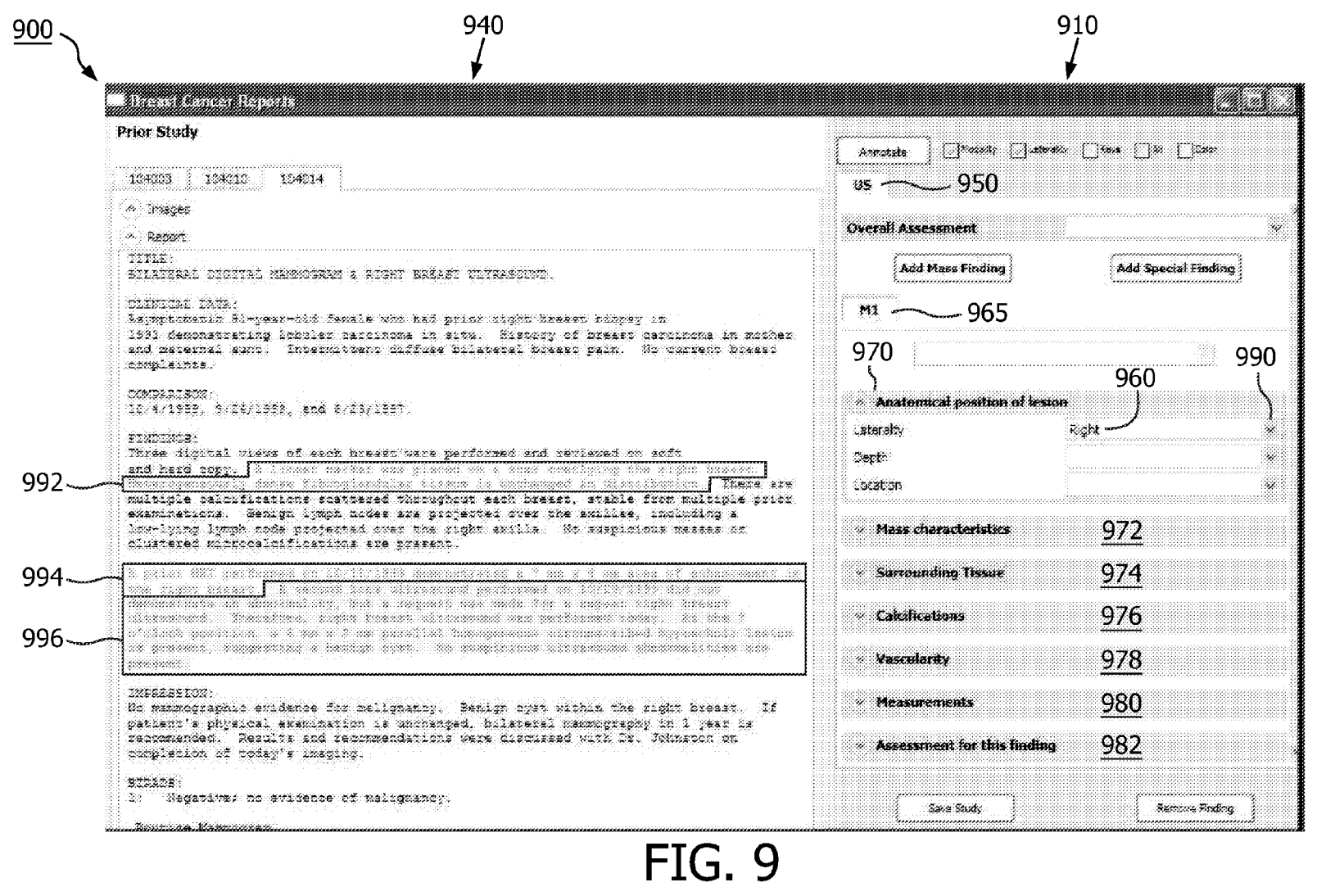

6. A GUI component highlights the sentence(s) with the highest relevance score. FIG. 9 illustrates a GUI 900 that includes, side by side, a BIRADS GUI 910 for selection of BIRADS descriptor(s) and/or finding(s), and a prior report 940 which may be selected by the user or automatically extracted from prior reports as described.

FIG. 9 illustrates a GUI 900 showing that on the selection of a BIRADS finding(s) in the system from a BIRADS GUI 910, the relevant text in a prior text report 940 is highlighted and shown side by side next to the current, reference, first or structured study 910 that includes BIRADS descriptors associated with the highlighted portions of the prior or unstructured report. Thus, in response to selecting a BIRADS finding including BIRADS selected or extracted descriptors such as modality 'US' 950 and laterality 'Right' 960, the relevant text in a prior text report is automatically highlighted. In FIG. 9, the BIRADS annotation of a lesion in an ultrasound 'US' image are included in tab 'M1' 965, and include a list of descriptor menus such as 'Anatomical position of lesion' 970, 'Mass characteristics' 972, 'Surrounding Tissue' 974, 'Calcification' 976, 'Vascularity' 978, 'Measurements' 980, and 'Assessment for this finding' 982. Upon selection of a menu, further descriptors are displayed for user selection, such as shown for the menu 'Anatomical position of lesion' 982, where descriptors such as 'Laterality,' 984 'Depth' 986 and 'Location' 988 are provided for further user selection of descriptors, where 'Right' 960 is selected from a further menu 990. As shown in FIG. 9, different portions of the prior report 940 may be highlighted differently. For example, finding with the same laterality are highlighted using a first color such as a foreground color, shown in FIG. 9 by a boxes 992, 994 that include 'right breast' shown in FIG. 9 as underlined by dashed lines, and ultrasound finding are low-lighted using a second color, such as a background color which is different from the first color, shown in FIG. 9 by a box 996 that includes 'ultrasound' shown in FIG. 9 as underlined by dashed lines.

Figure 10:
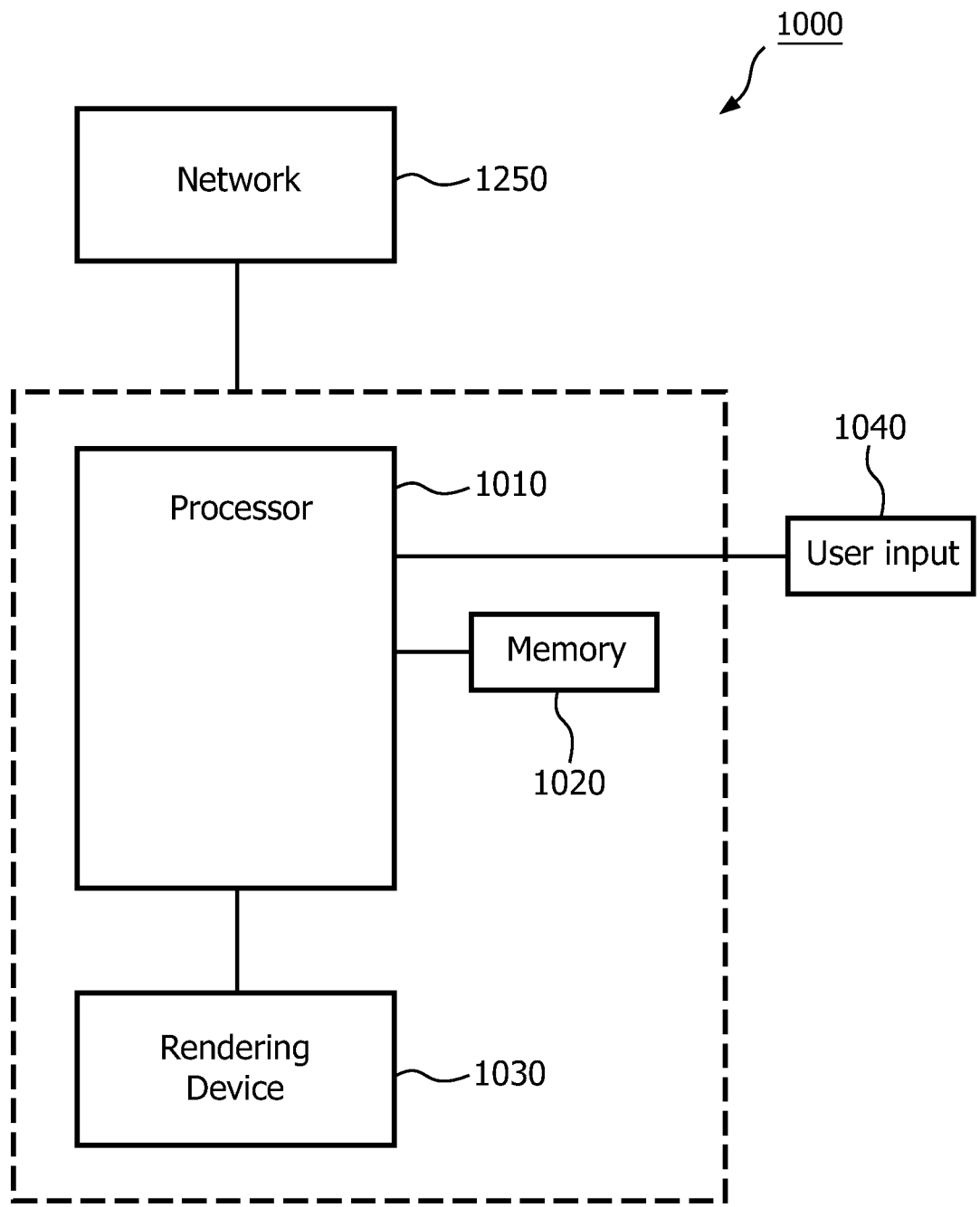
FIG. 10 shows a portion of a system in accordance with embodiments of the present system.

FIG. 10 shows a portion of a viewing system 1000 in accordance with embodiments of the present system. For example, a portion of the present system may include a processor 1010 operationally coupled to a memory 1020, a display 1030 and a user input device 1040. The memory 1020 may be any type of device for storing application data as well as other data related to the described operations. The application data and other data are received by the processor 1010 for configuring (e.g., programming) the processor 1010 to perform operation acts in accordance with the present system. The processor 1010 so configured becomes a special purpose machine particularly suited for performing in accordance with the present system.

The operation acts may include requesting, selecting, providing, and/or rendering of content such as displaying images annotated with structured descriptors, e.g., BIRADS descriptors and/or relevant free-text or unstructured text reports. The user input 1040 may include a keyboard, mouse, trackball or other device, including touch sensitive displays, which may be stand alone or be a part of a system, such as part of a personal computer, personal digital assistant, mobile phone, set top box, television or other device for communicating with the processor 1010 via any operable link. The user input device 1040 may be operable for interacting with the processor 1010 including enabling interaction within a UI as described herein. Clearly the processor 1010, the memory 1020, display 1030 and/or user input device 1040 may all or partly be a portion of a computer system or other device such as a client and/or server as described herein.

The methods of the present system are particularly suited to be carried out by a computer software program, such program containing modules corresponding to one or more of the individual steps or acts described and/or envisioned by the present system. Such program may of course be embodied in a computer-readable medium, such as an integrated chip, a peripheral device or memory, such as the memory 1020 or other memory coupled to the processor 1010. For example, the various components of the present system, such as the report analyzer, ontology engine, the reasoning and matching engine, UI and display engine, as well as the parser, mapper and stemmers may be software modules executed by the processor 1010, and/or hardware devices configured to perform the desired functions. Thus, the described components and modules of the present system may be implemented in software, hardware, firmware, some combination of software, hardware, and/or firmware; and/or otherwise implemented. The modules illustrated in FIGS. 3-5, and 7-8 4 may be co-located within a single processing unit. The processor 1010 may include multiple processing units, and some of these processing units may be located remotely from each other, where the various modules may be located remotely from the other modules and operative communication between the modules may be achieved via one or more wired and/or wireless communication links.

The program and/or program portions contained in the memory 1020 configure the processor 1010 to implement the methods, operational acts, and functions disclosed herein. The memories may be distributed, for example between the clients and/or servers, or local, and the processor 1010, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the processor 1010. With this definition, information accessible through a network 1250 and/or a server, is still within the memory, for instance, because the processor 1010 may retrieve the information from the network for operation in accordance with the present system, such as the various databases that may reside in servers, such as the ontology database or server 730, the syntactic rules database or server 840, and/or the medical ontology database or server 860.

The processor 1010 is operable for providing control signals and/or performing operations in response to input signals from the user input device 1040 as well as in response to other devices of a network and executing instructions stored in the memory 1020. The processor 1010 may be an application-specific or general-use integrated circuit(s). Further, the processor 1010 may be a dedicated processor for performing in accordance with the present system or may be a general-purpose processor wherein only one of many functions operates for performing in accordance with the present system. The processor 1010 may operate utilizing a program portion, multiple program segments, or may be a hardware device utilizing a dedicated or multi-purpose integrated circuit.

Although the present system has been described with reference to a medical system, e.g., MAM/US/MRI imaging system, it is also envisioned that the present system can be extended to other imaging, viewing, reporting and analysis systems and the like. Accordingly, the present system may be used to automatically find relevant free-text reports and highlight words and sentences related to structured descriptors selected by a user or automatically extracted from images that are annotated with such descriptors where all occurrences of a word is not highlighted, and only relevant occurrences are highlighted, as described.

Certain additional advantages and features of this invention may be apparent to those skilled in the art upon studying the disclosure, or may be experienced by persons employing the novel system and method of the present invention, chief of which is that a faster, easier and more reliable correlation among various reports having structured and/or or structured text or annotations, for example. Further variations of the present system would readily occur to a person of ordinary skill in the art and are encompassed by the following claims. Through operation of the present system, an automatic correlation is provided among different reports related to a common image, such as an image of a breast under examination where selecting desired descriptors, such as BIRADS descriptors, automatically results in finding relevant reports and highlighting relevant words and sentences in the obtained or found reports. In addition or alternatively, opening or selecting a report that includes descriptors that describe an image, and/or opening an image that includes annotated descriptors, automatically or in response to user action, such as a 'find' command, results in searching and finding relevant reports related to the selected image or report, as well as highlighting relevant words and sentences in the found reports that are related to the selected report including the descriptors.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present systems and methods, and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

In interpreting the appended claims, it should be understood that:

a) the word "comprising" does not exclude the presence of elements or acts other than those listed in a given claim;

b) the word "a" or "an" preceding an element does not exclude the presence of a plurality of such elements;

c) any reference signs in the claims do not limit their scope;

d) several "means" may be represented by the same item or by the same hardware- or software-implemented structure or function;

e) any of the disclosed elements may be comprised of hardware portions (e.g., including discrete and integrated electronic circuitry), software portions (e.g., computer programs), and any combination thereof;

f) hardware portions may be comprised of one or both of analog and digital portions;

g) any of the disclosed devices or portions thereof may be combined or separated into further portions unless specifically stated otherwise;

h) no specific sequence of acts or steps is intended to be required including an order of acts depicted in flow diagrams unless specifically indicated; and i) the term "plurality of" an element includes two or more of the claimed element, and does not imply any particular range or number of elements; that is, a plurality of elements may be as few as two elements, and may include an immeasurable number of elements.

What is claimed is:

1. A method for viewing a medical report describing radiological images, comprising the acts of:

opening a structured medical report describing one or more radiological images using descriptors selected from a predefined list of descriptors, wherein the descriptors of the structured medical report describe a first lesion and at least one descriptor includes an imaging modality of the one or more radiological images that include the described first lesion; and in response to the opening act, performing the further acts of:

searching by a processor for an unstructured further report of a prior study related to the descriptors of the structured medical report for a same patient, wherein the search matches keywords translated with an ontology from the descriptors of the structured medical report and an interpretation of one or more interpretations obtained from the free text of the unstructured further report, wherein the free text of the unstructured further report includes sentences and words in the sentences, wherein the interpretation of the one or more interpretations includes a plurality of attributes obtained from free text and describe a second lesion, wherein one attribute of the plurality of attributes includes an imaging modality of the image that includes the described second lesion in the unstructured further report, wherein the matching of the search comprises matching the imaging modality of the one attribute of the described second lesion obtained from the free text of the unstructured report with the imaging modality of the keyword translated from the at least one descriptor of the structured report, wherein the searching includes:
  determining a plurality of imaging modalities for the unstructured further report from headers in free text of the unstructured further report;
  determining one imaging modality selected from the plurality of imaging modalities for at least one sentence from the free text in the unstructured further report; and
  mapping words comprising the at least one sentence from the free text in the unstructured further report to at least a second one of the plurality of attributes of the interpretation identified by the determined one imaging modality; and highlighting in the free text of the unstructured further report of a prior study displayed on a display device at least one selected from a group comprising of the words in the sentences and the sentences of the one or more interpretations matched with keywords derived from the used descriptors of the structured medical report.

2. The method of claim 1, wherein the predefined list of descriptors include BIRADS descriptors, and the BIRADS descriptions identify an anatomical location of the described first lesion, wherein a keyword translated from the BIRADS descriptors includes a laterality of the identified anatomical location;
  wherein the free text used to obtain the plurality of attributes describing the described. second lesion in the free text of the unstructured further report of a prior study exclude BIRADS descriptors, wherein the plurality of attributes comprises the imaging modality and a laterality;
  wherein the matching comprises matching the laterality of the plurality of attributes of the described second lesion obtained from the free text of the unstructured report excluding BIRADS descriptors with the laterality of the keyword translated from the BIRADS descriptors of the structured report and matching the imaging modality of the at least one attribute of the described second lesion obtained from the free text of the unstructured report with the imaging modality of the keyword translated from BIRADS descriptors of the structured report.

3. The method of claim 1, wherein the at least second one of the plurality of attributes of one interpretation identified by the determined one imaging modality comprises a laterality.

4. The method of claim 1, wherein the free text of the unstructured report comprises a plurality of medical imaging modalities; and
  wherein the searching differentiates the sentences in the free text between the plurality of medical imaging modalities and the searching uses sentences in the free text that correspond to the imaging modality of the described second lesion to obtain a second attribute of the plurality of attributes, wherein the second attribute excludes the imaging modality of the described second lesion.

5. The method of claim 1, further comprising the act of:
  displaying simultaneously the structured medical report and the highlighted free text from the unstructured further report of a prior study of the same patient.

6. The method of claim 1, wherein the used descriptors are defined according to a hierarchical semantic network and stored in an XML data structure.

7. The method of claim 1, wherein the used descriptors are automatically extracted from the structured medical report in response to the opening act.

8. The method of claim 1, wherein the structured medical report includes an image annotated with the used descriptors, and the used descriptors are automatically extracted from the image in response to the opening act.

9. The method of claim 1, wherein free text of the unstructured further report includes unrestricted words.

10. A computer program product including computer data stored on a non-transitory computer readable medium, the computer program product comprising program code configured to perform the method of claim 1.

11. A report viewer comprising a processor configured to perform the acts of:
  opening a structured medical report that describes radiological images using descriptors selected from a predefined list of descriptors, wherein the descriptors of the structured medical report describe a first lesion and the descriptors comprise an imaging modality of at least one of the radiological images that include the described first lesion and the descriptors comprise an anatomical location of the described first lesion; and
  in response to the opening act, performing the further acts of:
  searching for an unstructured further report of a prior study of the same patient related to the descriptors of the structured medical report,
  wherein the search matches keywords translated with an ontology from the descriptors of the structured medical report and an interpretation of one or more interpretations obtained from free text of the unstructured further report,
  wherein the free text of the unstructured further report includes sentences and words in the sentences,
  wherein the interpretation includes a plurality of attributes obtained from the free text and describe a second lesion,
  wherein the plurality of attributes includes an anatomical position of the described second lesion and an imaging modality of the image that includes the described second lesion in the unstructured further report,
  wherein the matching of the search comprises matching the anatomical position and the imaging modality of the plurality of attributes of the described second lesion obtained from the free text of the unstructured report with the anatomical position and imaging modality of the keywords translated from the descriptors describing the described first lesion of the structured report,
  wherein the searching includes:
  determining a plurality of imaging modalities for the unstructured further report from headers in the free text of the unstructured further report;
  determining one imaging modality selected from the plurality of imaging modalities for at least one sentence from the free text in the unstructured further report; and
  mapping words comprising the at least one sentence from the free text in the unstructured further report to at least a second one of the plurality of attributes of the interpretation identified by the determined one imaging modality; and
  highlighting in the free text of the unstructured further report of a prior study of the same patient displayed on a display device at least one selected from a group comprising of the words in the sentences and the sentences of the one or more interpretations matched with keywords derived from the descriptors of the structured medical report.

12. The report viewer of claim 11, wherein the predefined list of descriptors include BIRADS descriptors and the keywords further include the imaging modality and a laterality of an anatomical position of the described first lesion;
wherein the free text of the unstructured report excludes BIRADS descriptors;
wherein the searching comprises obtaining the plurality of attributes describing the second described lesion which include the modality and a laterality obtained from the free text;
wherein the matching of the search comprises matching the modality and the laterality translated from the BIRADS descriptors describing the first lesion to the modality and laterality of the plurality of attributes obtained from the free text excluding BIRADS descriptors that describe the second described lesion in the unstructured further report of a prior study.

13. The report viewer of claim 11, wherein the processor is further configured to;
segment the unstructured further report into sections;
identify sentences in the sections; and
group words in the sentences to form grouped words for each sentence; and
determine the one imaging modality selected from the plurality of imaging modalities for at least one sentence from the free text in the grouped words.

14. The report viewer of claim 11, wherein the at least second one of the plurality of attributes of one interpretation identified by the determined one imaging modality comprises a laterality.

15. The report viewer of claim 11, wherein the processor is further configured to:
simultaneously display the structured medical report and the highlighted free text from the unstructured further report.

16. The report viewer of claim 11, wherein the processor is further configured to:
the used descriptors are defined according to a hierarchical semantic network and stored in an XML data structure.

17. The report viewer of claim 11, wherein the processor is further configured to automatically extract the descriptors from the medical report in response to the opening act.

18. A non-transitory computer readable medium encoded with a computer program, which, when executed by a processor of a computer causes the computer to:
open a structured medical report describing one or more radiological images using descriptors selected from a predefined list of descriptors, wherein the descriptors of the structured medical report describe a first lesion and at least one descriptor includes an imaging modality of the one or more radiological images that include the described first lesion; and
search for an unstructured further report of a prior study related to the descriptors of the structured medical report for a same patient,
wherein the search matches keywords translated with an ontology from the descriptors of the structured medical report and an interpretation of one or more interpretations obtained from free text of the unstructured further report,
wherein the free text of the unstructured further report includes sentences and words in the sentences,
wherein the interpretation of the one or more interpretations includes a plurality of attributes obtained from the free text and describe a second lesion,
wherein one attribute of the plurality of attributes includes an imaging modality of the image that includes the described second lesion in the unstructured further report,
wherein the matching of the search comprises matching the imaging modality of the one attribute of the described second lesion obtained from the free text of the unstructured report with the imaging modality of the keyword translated from the at least one descriptor of the structured report,
wherein the searching includes:
determining, a plurality of imaging modalities for the unstructured further report from headers in the free text of the unstructured further report;
determining one imaging modality selected from the plurality of imaging modalities for at least one sentence from the free text in the unstructured further report; and
mapping words comprising the at least one sentence from the free text in the unstructured further report to at least a second one of the plurality of attributes of the interpretation identified by the determined one imaging modality; and
highlight in the free text of the unstructured further report of a prior study displayed on a display device at least one selected from a group comprising of the words in the sentences and the sentences of the one or more interpretations matched with keywords derived from the used descriptors of the structured medical report.

19. The non-transitory computer readable medium of claim 18, wherein the at least second one of the plurality of attributes of one interpretation identified by the determined one imaging modality comprises a laterality.

20. The non-transitory computer readable medium of claim 18, wherein the computer program further causes the processor to:
segment the unstructured further report into sections;
identify sentences in the sections; and
group words in the sentences to form grouped words for each sentence; and
determine the one imaging modality selected from the plurality of imaging modalities for at least one sentence from the free text in the grouped word.

* * * * *